United States Patent
Burkholz

(10) Patent No.: US 10,576,250 B2
(45) Date of Patent: Mar. 3, 2020

(54) SECUREMENT DRESSING FOR VASCULAR ACCESS DEVICE WITH SKIN ADHESIVE APPLICATION WINDOW

(71) Applicant: Becton, Dickinson and Company, Franklin Lakes, NJ (US)

(72) Inventor: Jonathan Karl Burkholz, Salt Lake City, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 247 days.

(21) Appl. No.: 15/377,148

(22) Filed: Dec. 13, 2016

(65) Prior Publication Data

US 2018/0161543 A1 Jun. 14, 2018

(51) Int. Cl.
*A61M 25/02* (2006.01)
*A61F 13/00* (2006.01)

(52) U.S. Cl.
CPC ... *A61M 25/02* (2013.01); *A61F 2013/00412* (2013.01); *A61M 2025/0266* (2013.01); *A61M 2025/0273* (2013.01); *A61M 2205/0205* (2013.01)

(58) Field of Classification Search
CPC . A61F 2013/00412; A61M 2025/0273; A61M 2205/0205; A61M 25/02; A61M 2025/0246; A61M 2025/0252; A61M 2025/026; A61B 46/23; A61B 2046/234
See application file for complete search history.

(56) References Cited

U.S. PATENT DOCUMENTS

| | | | |
|---|---|---|---|
| 4,059,105 A | 11/1977 | Cutruzzula |
| 4,324,237 A | 4/1982 | Buttaravoli |
| 4,584,192 A | 4/1986 | Dell et al. |
| 4,716,032 A | 12/1987 | Westfall et al. |
| 4,915,934 A | 4/1990 | Tomlinson |
| 4,925,668 A | 5/1990 | Khan et al. |
| 5,023,082 A | 6/1991 | Friedman et al. |
| 5,512,199 A | 4/1996 | Khan et al. |
| 5,547,662 A | 8/1996 | Khan et al. |

(Continued)

FOREIGN PATENT DOCUMENTS

| | | |
|---|---|---|
| FR | 3018453 | 9/2015 |
| WO | 02/058774 | 8/2002 |
| WO | 2015/035238 | 3/2015 |

OTHER PUBLICATIONS

"ChloraPrep," Enturia, Retrieved from the Internet URL: http://www.enturia.com/products/chloraPrep/chloraPrep-product.html, on Oct. 31, 2008, p. 1-3.

(Continued)

*Primary Examiner* — Deanna K Hall
(74) *Attorney, Agent, or Firm* — Kirton & McConkie; Craig Metcalf; Kevin Stinger

(57) ABSTRACT

Catheter securement dressings that aid in applying skin adhesive to a catheter insertion site are described. Catheter securement dressings can include a first dressing layer that secures a position of a catheter at a catheter insertion site following catheterization. The first dressing layer can include an access window that provides access to the catheter insertion site to allow for application of skin adhesive to the catheter insertion site. After the skin adhesive has dried, a second dressing layer can be folded over the first dressing layer to cover the access window.

5 Claims, 6 Drawing Sheets

(56) References Cited

U.S. PATENT DOCUMENTS

| | | | |
|---|---|---|---|
| 5,616,338 | A | 4/1997 | Fox, Jr. et al. |
| 5,637,098 | A | 6/1997 | Bierman |
| 5,861,440 | A | 1/1999 | Gohla et al. |
| 6,051,609 | A | 4/2000 | Yu et al. |
| 6,337,357 | B1 | 1/2002 | Fukunishi et al. |
| 6,413,539 | B1 | 7/2002 | Shalaby |
| 6,488,942 | B1 | 12/2002 | Ingemann |
| 6,846,846 | B2 | 1/2005 | Modak et al. |
| 6,861,060 | B1 | 3/2005 | Luriya et al. |
| 7,198,800 | B1 | 4/2007 | Ko |
| 7,268,165 | B2 | 9/2007 | Greten et al. |
| 7,651,479 | B2 | 1/2010 | Bierman |
| 7,699,810 | B2 | 4/2010 | Rosenberg |
| 7,704,935 | B1 | 4/2010 | Davis et al. |
| 8,679,066 | B2 | 3/2014 | Aviles |
| 2001/0016589 | A1 | 8/2001 | Modak et al. |
| 2002/0144705 | A1 | 10/2002 | Brattesani et al. |
| 2003/0072781 | A1 | 4/2003 | Pelerin |
| 2003/0162839 | A1 | 8/2003 | Symington et al. |
| 2004/0039349 | A1 | 2/2004 | Modak et al. |
| 2006/0095008 | A1 | 5/2006 | Lampropoulos et al. |
| 2006/0165751 | A1 | 7/2006 | Chudzik et al. |
| 2006/0239954 | A1 | 10/2006 | Sancho |
| 2008/0075761 | A1 | 3/2008 | Modak et al. |
| 2008/0182921 | A1 | 7/2008 | Suh et al. |
| 2009/0143740 | A1 | 6/2009 | Bierman et al. |
| 2011/0060295 | A1 | 3/2011 | Hen et al. |
| 2013/0150796 | A1 | 6/2013 | Souza et al. |
| 2014/0257242 | A1 | 9/2014 | Sung et al. |
| 2015/0032057 | A1 | 1/2015 | Ashfaque |
| 2015/0224285 | A1* | 8/2015 | Howell ............... A61M 25/02 |
| | | | 604/180 |
| 2016/0193452 | A1 | 7/2016 | Hanson et al. |

OTHER PUBLICATIONS

"Preoperative Skin Preparation and Peri operative Oral Care for the Short-Term Ventilated Patient," Sage Products, Inc., Retrieved from the internet URL: http://www.sageproducts.com/products/ssi-vap-prevention.cfm, on Oct. 31, 2008, p. 1.

"Address Multi-Drug Resistant Organisms on the Skin with Early Preop Prep," Sage Products, Inc., Retrieved from the Internet URL: http://www.sageproducts.com/products/ssi-prevention.cfm, on Oct. 31, 2008, p. 1.

"Preoperative Skin Preparation for the Surgical Patient," Sage Products, Inc., Retrieved from the internet URL: http://www.sageproducts.com/products/skin-prep.cfm, on Oct. 31, 2008, p. 1.

"Clinell Alcoholic 2% Chlorhexidine," Gama Healthcare, Retrieved from the Internet URL: http://www.gamahealthcare.com/clinellaca2c.html, on Nov. 7, 2008, p. 1-3.

* cited by examiner

SECUREMENT DRESSING FOR VASCULAR ACCESS DEVICE WITH SKIN ADHESIVE APPLICATION WINDOW

BACKGROUND OF THE INVENTION

This disclosure relates generally to intravenous catheters (e.g., vascular access devices). More specifically, this application discloses various methods for using and systems of securement dressings for vascular access devices with skin adhesive application windows. In general, vascular access devices are inserted into veins via peripheral or central vessels for diagnostic or therapeutic reasons. Vascular access devices can be used for infusing fluid (e.g., saline solution, blood, medicaments, and/or total parenteral nutrition) into a patient, withdrawing fluids (e.g., blood) from a patient, and/or monitoring various parameters of the patient's vascular system.

Intravenous (IV) catheter assemblies are among the various types of vascular access devices. Over-the-needle peripheral IV catheters are a common IV catheter configuration. As its name implies, an over-the-needle catheter is mounted over an introducer needle having a sharp distal tip. The introducer needle is generally a venipuncture needle coupled to a needle assembly that helps guide the needle and facilitates its cooperation with the catheter. At least the inner surface of the distal portion of the catheter tightly engages the outer surface of the needle to prevent peelback of the catheter and, thereby, to facilitate insertion of the catheter into the blood vessel. The catheter and the introducer needle are often assembled so that the sharp distal tip of the introducer needle extends beyond the distal tip of the catheter. Moreover, the catheter and needle are often assembled so that during insertion, the bevel of the needle faces up, away from the patient's skin. The catheter and introducer needle are generally inserted at a shallow angle through the patient's skin into a blood vessel.

Following catheterization, the intravenous catheter assembly is secured to the patient to prevent premature and/or unintended removal. Often a securement dressing is applied to the catheter insertion site to secure the catheter assembly to the patient. The securement dressing limits exposure to the catheter site, prevents contamination of the catheter site, and prevents premature and/or unintended removal of the catheter. Increasingly, skin adhesives are also applied to the catheter insertion site to further secure the intravenous catheter assembly, to seal the catheter insertion site, and/or to lengthen the time that the catheter can stay in place. Skin adhesives are not designed to replace the securement dressing, but rather to locally seal the insertion site around the catheter, to provide localized securement of the catheter at the point of insertion and in some cases provide securement to the overall catheter assembly.

Although conventional securement dressings and skin adhesives may provide a variety of benefits, they are not without their shortcomings. For example, current adhesives require time to dry before a securement dressing can be applied. This means that a clinician must first insert the catheter, and then while holding the inserted catheter in place with one hand, must use the other hand to open the adhesive container, apply the adhesive, wait for the adhesive to dry, prepare the securement dressing, and place the securement dressing. Carrying out these multiple steps while holding the catheter in place may be difficult and may result in messy and/or ineffective application of the adhesive, use of too much adhesive that can require a lengthy cleanup process for removal, inadvertent adhering of the clinician's glove or fingers to the catheter device or patient, and/or unintentional dislodging of the catheter.

Thus, while a variety of securement dressings currently exist, challenges still exist, including those listed above. Accordingly it would be an improvement in the art to augment or even replace current systems and techniques with other systems and techniques.

BRIEF SUMMARY OF THE INVENTION

This disclosure relates generally to catheter securement dressings that aid in applying skin adhesive to a catheter insertion site. More specifically, this disclosure discusses methods and systems for securing a catheter at a catheter insertion site to permit a clinician to apply skin adhesive to the catheter insertion site while reducing the risk of dislodging the catheter during application, allowing for efficient application of the skin adhesive, and reducing the use of excess adhesive.

Some exemplary catheter securement dressings can comprise a first dressing layer comprising an access window, a first adhesive layer configured to adhere the first dressing layer to skin, a second dressing layer, and a second adhesive layer configured to adhere the second dressing layer to the first dressing layer. The catheter securement can also include a first overlap portion of the first dressing layer selectively coupled to a second overlap portion of the second dressing layer. The second dressing layer can comprise a fold line.

In some embodiments, the catheter securement dressing further comprises a bottom release liner covering the first adhesive layer. The catheter securement dressing can also include a second release liner covering the second adhesive layer. The catheter securement dressing can also comprise a top release liner covering a portion of the first dressing layer. The top release liner can comprise a top access window that overlaps at least in part with the access window. In some cases, the access window can comprise one or more of a mesh support and a slotted opening. In other cases, at least one of the first and second adhesive layers can include an antimicrobial agent.

In some embodiments, the methods include a method of applying a catheter securement comprising inserting a catheter at a catheter insertion site, attaching a first dressing layer of a catheter securement at the catheter insertion site, applying skin adhesive to the catheter insertion site through an access window in the first dressing layer, and attaching a second dressing layer of the catheter securement over the access window. The methods can also include attaching the first dressing layer to secure the catheter at the catheter insertion site to prevent dislodging of the catheter during application of the skin adhesive. The methods can include removing a top release liner from the first dressing layer after applying the skin adhesive. The methods can comprise removing a bottom release liner from an adhesive layer of the first dressing layer prior to attaching the first dressing layer at the catheter insertion site. Also, the methods can comprise removing a second release liner from an adhesive layer of the second dressing layer prior to attaching the second dressing layer over the access window.

In some embodiments, the catheter securement dressings comprise a first dressing layer comprising a first overlap portion, a second dressing layer comprising a second overlap portion, and an access window formed in the first dressing layer, where the first overlap portion is selectively coupled to the second overlap portion. In some instances, the second dressing layer comprises a fold line configured to permit the second dressing layer to fold away from the first dressing layer to uncover the access window. In other instances, the first dressing layer can comprise a first adhesive layer configured to attach to skin of a patient. In yet other instances the second dressing layer can comprise a second adhesive layer configured to attach the second dressing layer over the access window. The catheter securement dressings can further comprise a top release liner disposed on a top surface of the first dressing layer. The top release liner can comprise a top access window that overlaps at least in part with the access window.

BRIEF DESCRIPTION OF THE SEVERAL VIEWS OF THE DRAWINGS

In order that the manner in which the above-recited and other features and advantages of disclosed embodiments are obtained and will be readily understood, a more particular description of the systems and methods briefly described above will be rendered by reference to specific embodiments thereof, which are illustrated in the appended drawings. Understanding that these drawings depict only typical embodiments and are not, therefore, to be considered to be limiting of its scope. Exemplary embodiments of the disclosed systems and methods will be described and explained with additional specificity and detail below through the use of the accompanying drawings in which.

Figure 1:
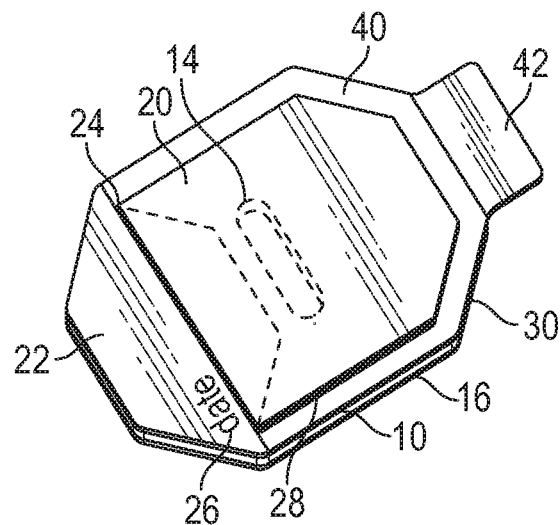
FIG. 1 illustrates a perspective view of an exemplary catheter securement dressing with a skin adhesive application window.

The Figures illustrate specific aspects of exemplary catheter securement dressing and methods for making and using such devices as described below. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices. Moreover, the Figures may show simplified or partial views, and the dimensions of elements in the Figures may be exaggerated or otherwise not in proportion for clarity and instruction.

DETAILED DESCRIPTION OF THE INVENTION

The following description supplies specific details in order to provide a thorough understanding. Nevertheless, the skilled artisan would understand that the described catheter securement dressings and methods of making and using them can be implemented and used without employing these specific details. Indeed, the catheter securement dressing and associated methods can be placed into practice by modifying the illustrated devices and methods and can be used in conjunction with any other apparatus and techniques conventionally used in the industry.

In general, this disclosure is related to systems and methods for securing an intravenous catheter assembly to a patient following catheterization. In some instances, a catheter securement dressing can comprise one or more adhesive portions which are configured to secure a position of the catheter following catheterization. In some embodiments, the catheter is inserted at the catheter insertion site and then the catheter securement dressing is applied to secure the catheter. After the catheter is secured by an adhesive portion of a first dressing layer, a skin adhesive can be applied to the catheter insertion site through an access window in the first dressing layer of the catheter securement dressing. After the skin adhesive is applied, a second dressing layer of the catheter securement dressing can be folded onto the first dressing layer to further secure and/or protect the catheter insertion site. The skin adhesive can be allowed to dry before the second dressing layer is folded onto the first dressing layer, or the second dressing layer can be folded onto the first dressing layer immediately after the skin adhesive is applied or while the skin adhesive is drying. The catheter securement dressing can be configured to aid the clinician by securing the catheter at the catheter insertion site while the clinician applies skin adhesive to the catheter insertion site to provide localized securement of the catheter at the point of insertion. The catheter securement dressing can be configured to help limit the overspreading of the skin adhesive during application and can focus the application of the skin adhesive to an area immediately around the catheter insertion site.

Figure 2:
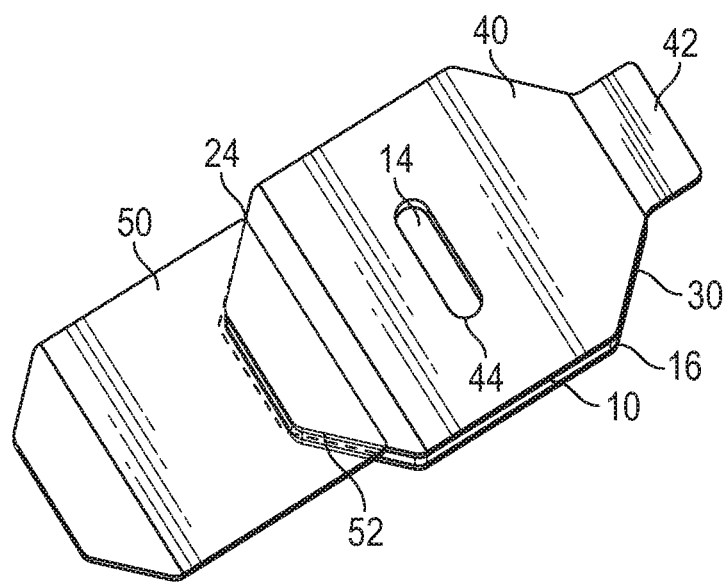
FIG. 2 illustrates a perspective view of the catheter securement dressing of FIG. 1.
Figure 3:
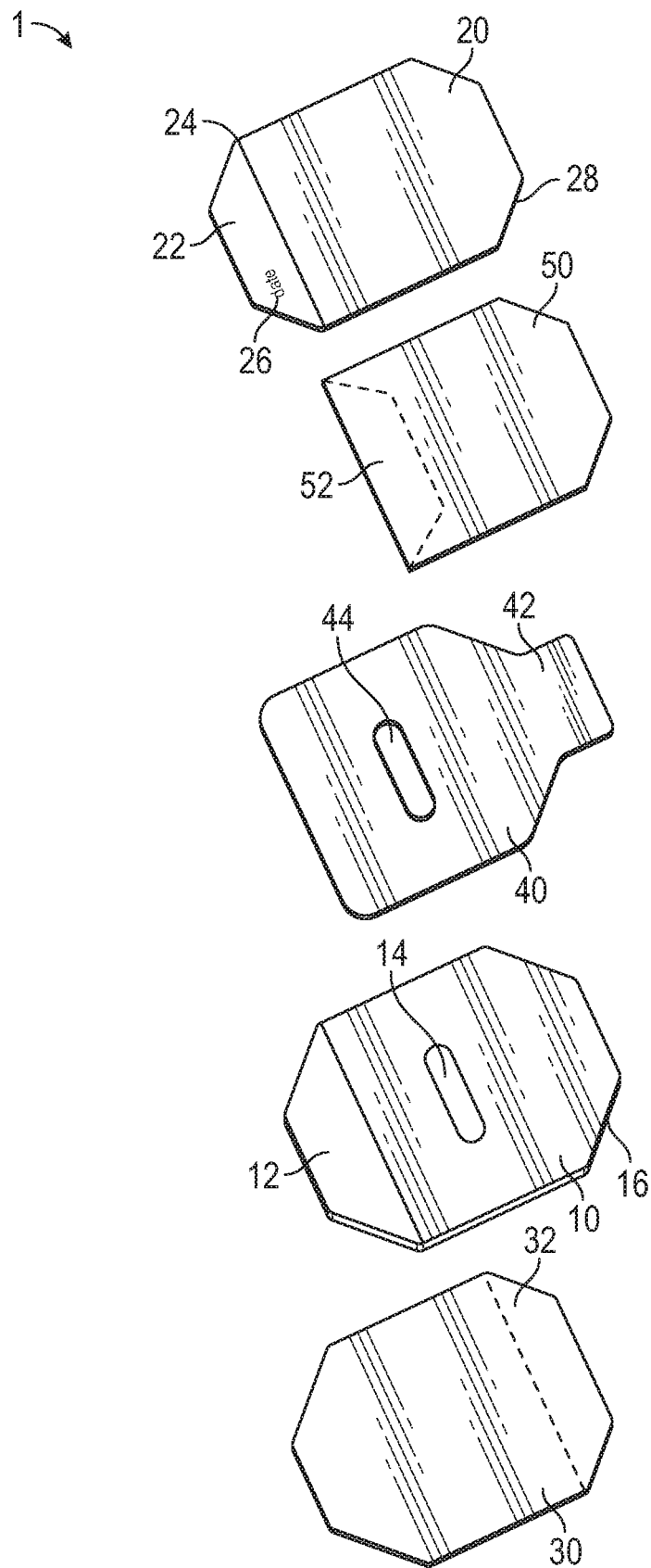
FIG. 3 illustrates a perspective exploded view of the catheter securement dressing of FIG. 1.

Referring now to FIGS. 1-3, a catheter securement dressing 1 is shown. The catheter securement dressing 1 can comprise a first dressing layer 10. The first dressing layer 10 can comprise a first overlap portion 12 at a first end. The first dressing layer 10 can also comprise an access window 14 configured to permit access to a catheter insertion site. The first dressing layer 10 can include an adhesive layer 16 on a bottom contact side of the first dressing layer 10 for contact and adhesion with a skin surface of a patient. The catheter securement dressing 1 can also comprise a second dressing layer 20. In some embodiments, the second dressing layer 20 is selectively coupled to the first dressing layer via a second overlap portion 22 that is selectively coupled to the first overlap portion 12. The first overlap portion 12 and second overlap portion 22 can be selectively coupled in any manner suitable to allow the catheter securement dressing 1 to function as intended. For example, the first overlap portion 12 and the second overlap portion 22 can be selectively coupled by an adhesive, by welding, by stitching, by one or more fasteners (e.g., brads, grommets, staples, clips, etc.), or by any other suitable manner.

The second dressing layer 20 can also comprise a fold line 24 that permits the second dressing layer 20 to fold back along fold line 24 to uncover the access window 14. The second dressing layer 20 can also comprise a label area 26 where a clinician can note relevant information, such as the time and/or date when the catheter securement dressing 1 was applied to the patient. The second dressing layer 20 can also comprise an adhesive layer 28 on a bottom contact surface of the second dressing layer 20 for contact and adhesion with a top surface of the first dressing layer 10.

In some embodiments, the access window 14 is configured to be placed over at least a portion of the catheter insertion site and to provide access to at least a portion of the catheter insertion site. Access window 14 may be an opening such as a window or may be a slit or strip opening in the first dressing layer 10. While the access window 14 may be configured with any suitable shape that permits access to at least a portion of the catheter insertion site, at least in some embodiments, the access window may be a rounded rectangle as shown in the Figures, or it may be a square, a triangle, a polygon, an oval, a cross-shape, an X-shape, a cardioid, a lenticular shape, or any other shape suitable to permit access to at least a portion of the catheter insertion site when the catheter securement dressing 1 is applied to the patient.

The first dressing layer 10 can also comprise a bottom release liner 30 configured to protect adhesive layer 16 from inadvertent and premature adhesion before the catheter securement dressing 1 is ready to be applied to the patient, as is described in further detail below. The bottom release liner 30 can be provided with a bottom release tab 32 configured to aid a clinician in removing the bottom release liner 30 when the clinician is ready to apply the catheter securement dressing 1. The bottom release liner 30 may be placed over the adhesive portion 16 to preserve adhesive properties and to preserve sterility. In some embodiments, the bottom release liner 30 comprises protective packaging within which the catheter securement dressing 1 is packaged.

In some embodiments, the first dressing layer 10 includes a top release liner 40. The top release liner 40 can be provided to preserve sterility and/or cleanliness of the top surface of the first dressing layer 10. The top release liner 40 can also be provided to prevent excess skin adhesive from adhering to the first dressing layer 10, as described in more detail below. The top release liner 40 can be provided with a top release tab 42 configured to aid the clinician in removing the top release liner 40 from the first dressing layer 10. The top release tab can be disposed on any portion of the top release liner 40 that can aid the clinician in removing the top release liner 40 from the first dressing layer 10. The top release liner 40 can also be provided with a top access window 44 configured to provide access to at least a portion of the catheter insertion site. While the top access window 44 can be shaped in any suitable fashion that permits access to at least a portion of the catheter insertion site, at least in some embodiments the top access window 44 comprises the same shape as the access window 14.

In some embodiments, the second dressing layer 20 comprises a second release liner 50. The second release liner 50 can be provided to preserve sterility and/or cleanliness of a bottom surface of the second dressing layer 20 at a contact interface between the first dressing layer 10 and the second dressing layer 20. The second release liner 50 can also be provided to protect the adhesive layer 28 from inadvertent and premature adhesion during application of the catheter securement dressing 1 to the patient. The second release liner 50 can comprise a second release tab 52 configured to aid the clinician in removing the second release liner 50 from the second dressing layer 20. In some instances, the second release tab 52 can be disposed along the fold line 24. In other instances, the second release tab 52 can be disposed on any portion of the second release liner 50 that can aid the clinician in removing the second release liner 50 from the second dressing layer 20. In yet other instances, one or more additional release liners can be provided to preserve sterility and/or cleanliness of any surface of the catheter securement dressing 1 and/or to prevent inadvertent and premature adhesion before the catheter securement dressing 1 is ready to be applied to the patient. In some cases, a single release liner can be used between the first dressing layer 10 and the second dressing layer 20. For example, the top release liner 40 can be used and the second release liner 50 can be omitted. Likewise, the top release liner 40 can be omitted and the second release liner 50 can be used. In other cases, a single release liner comprising one or more features of both the top release liner 40 and the second release liner 50 can be used.

The adhesive layers 16, 28 can comprise any type or form of adhesive that is suitable for use with the systems and methods described herein. In some cases, the adhesive layers 16, 28 can comprise one or more of spray-on adhesive, adhesive film, contact adhesive, and pressure sensitive adhesive. For example, the adhesive layer 16 can comprise a polymer-based pressure sensitive adhesive that forms a bond between the adhesive layer 16 and a surface of the patient's skin when the clinician applies the first dressing layer 10 to the patient's skin and applies light pressure. Likewise, the adhesive layer 28 can comprise a polymer-based pressure sensitive adhesive that forms a bond between the adhesive layer 28 and the top surface of the first dressing layer 20 when the clinician folds the second dressing layer 20 against the first dressing layer 10 and applies light pressure. The adhesive layer 16 can further include a slight liquid carrier that facilitates bonding with skin. In some instances, the adhesive layer 16 can include a single-use glue, such that the adhesive loses its adhesive properties once removed from the skin.

In some embodiments, the adhesive layers 16, 28 comprise a multiple-use adhesive, wherein the multiple-use adhesive allows the adhesive layer to be applied and removed repeatedly. For example, a multiple-use adhesive for adhesive layer 16 can be desired to permit removal, realignment, and/or reapplication of the catheter securement dressing 1 against the surface of the patient's skin. Similarly, a multiple-use adhesive for adhesive layer 28 can be desired to permit the second dressing layer 20 to be folded back from the first dressing layer 10 to permit inspection of the catheter insertion site (e.g., to inspect the catheter insertion site to determine if the tip of the catheter has become occluded within the vein). In some embodiments, the adhesive layers 16, 28 are formed in any shape, pattern, size and/or configuration necessary to provide a desired securement between the catheter securement dressing 1 and the skin of the patient, and between the first dressing layer 10 and the second dressing layer 20.

In some embodiments, the adhesive layers 16, 28 also include one or more anti-microbial agents. For example, the adhesive layers 16, 28 can include one or more anti-microbial agents to aid in maintaining sterility at the catheter insertion site. The anti-microbial agents can include any suitable agent for maintaining sterility at the catheter insertion site. In some cases, the anti-microbial agents can include a topical disinfectant such as chlorhexidine gluconate or chlorhexidine di-acetate. Other suitable anti-microbial agents include, but are not limited to, silver-based agents, Triclosan, chloroxylenol (PCMX), BEC, BAC, Octenidine, and other antibiotics. In other cases, the adhesive layer 28 can comprise an antimicrobial adhesive zone 29 (shown in FIG. 9) that is configured to overlap the access window 14 and to contact the catheter insertion site. The antimicrobial adhesive zone 29 can comprise one or more adhesives as described and one or more antimicrobial agents as described.

The release liners 30, 50 can comprise any material or combination of materials that permit temporary bonding between the release liners 30, 50 and the adhesive layers 16, 28, wherein upon removal of the release liners 30, 50, the adhesive layers 16, 28 are left undisturbed. Non-limiting examples of compatible materials for release liners 30, 50 include plastic film, paper, plastic, metal foil, plastic coated paper, wax coated paper, wax coated plastic, plastic coated foil, and wax coated foil. Additionally, the release liners 30, 50 can be coated, impregnated, or layered with one or more of a release agent and an anti-microbial agent. In some embodiments, only on a portion of release liners 30, 50 in contact with the adhesive layers 16, 28 have the release properties or agents, and in other embodiments, release liners 30, 50 have the same manufacture throughout.

In some embodiments, the dressing layers 10, 20 comprise any suitable dress and/or wound management material for use in securing catheter insertion sites. For example, the dressing layers 10, 20 can comprise transparent polyurethane dressings, gauze dressings, moisture reactive dressings, or any other suitable material for securing catheter insertion sites. The dressing layers 10, 20 can also comprise any suitable antimicrobial material, including those described above. The dressing layers 10, 20 can also comprise any thickness suitable for securing catheter insertion sites.

Figure 4:
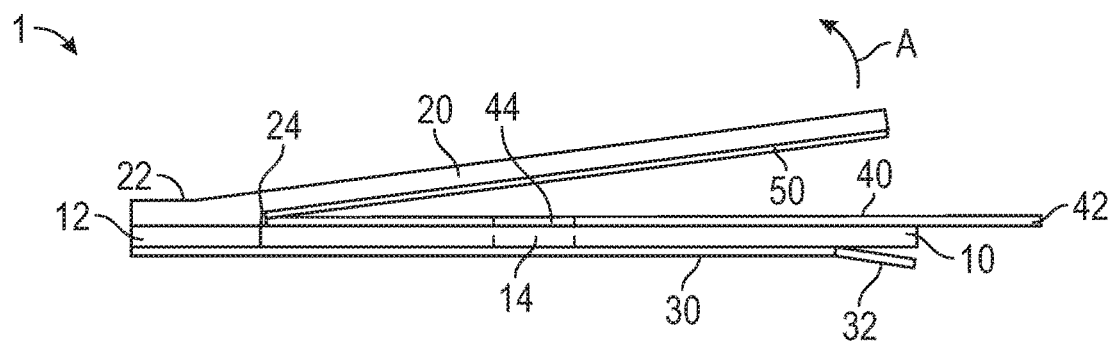
FIG. 4 illustrates a side view of the catheter securement dressing of FIG. 1.

Referring now to FIG. 4, a side view of the catheter securement dressing 1 is illustrated. As shown in FIG. 4, the catheter securement dressing 1 can comprise a first dressing layer 10 selectively coupled at the overlap portion 12 to a second dressing layer 20. The overlap portion 12 can be selectively coupled to the second overlap 22. The second dressing layer 20 can be configured to fold back in the direction indicated by arrow A along the fold line 24. The fold line 24 can be formed as a thinner, scored, or otherwise weakened portion in the second dressing layer 20. The second dressing layer 20 can also be configured to refold into position over the first dressing layer 10 along the fold line 24. As described above and shown in FIG. 4, the release liners 30, 40 can be disposed on a bottom and top surface of the first dressing layer, respectively. Similarly, release tabs 32, 42 can be disposed to aid the clinician in removing the respective release liners 30, 50. The second release liner 50 can also be disposed on a bottom surface of the second release liner 20 and release tab 52 can facilitate removal of the second release liner 50.

Figure 5:
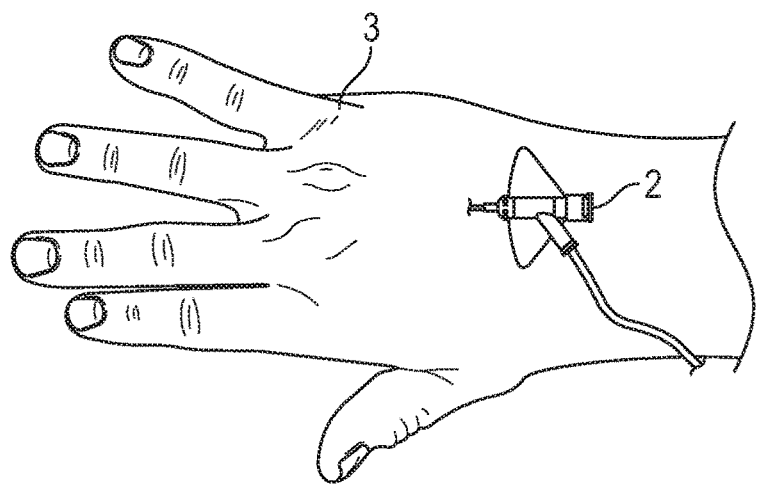
FIGS. 5-10 illustrate a top view of the catheter securement dressing of FIG. 1 placed on a hand of a patient in successive stages of insertion of a catheter, application of the catheter securement dressing, and application of a skin adhesive.
Figure 6:
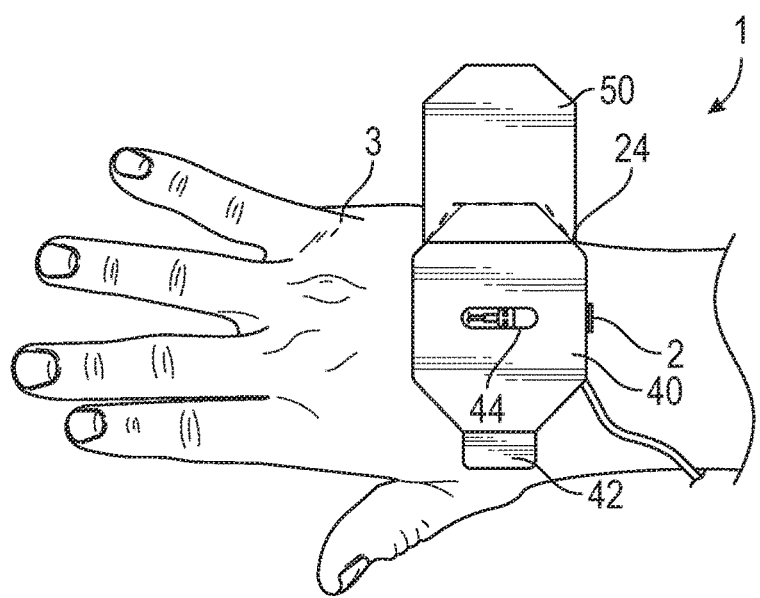

Referring now to FIGS. 5-10, the catheter securement dressing 1 can be applied after a catheter 2 has been inserted into the skin of the patient 3. In some embodiments, applying the catheter securement dressing 1 includes cleaning and preparing the catheter insertion site by the clinician. Once the site on the patient 3 is prepared, the catheter 2 can be inserted at the catheter insertion site as shown in FIG. 5. The catheter 2 can be inserted into any suitable portion of the patient 3, including, but not limited to, a dorsal surface of the hand. As shown in FIG. 6, the second dressing layer 20 can be folded back along fold line 24 to uncover the top release liner 40. The clinician can locate the catheter insertion site through the top access window 44 and can apply the catheter securement dressing 1 over the catheter insertion site after the bottom release liner 30 has been removed. The first dressing layer 10 can then be pressed onto the skin of the patient so that adhesive layer 16 attaches the bottom portion of the first dressing layer 10 to the skin of the patient 3 to secure the catheter 2 to the patient 3. In embodiments where the bottom release liner 30 comprises protective packaging, the protective packaging can be removed prior to application of the catheter securement dressing 1 to expose adhesive layer 16.

Figure 7:
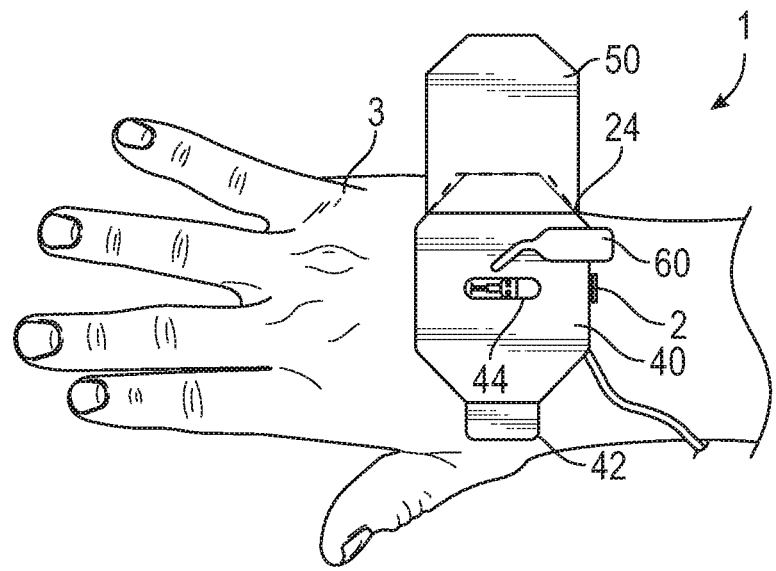
Figure 8:
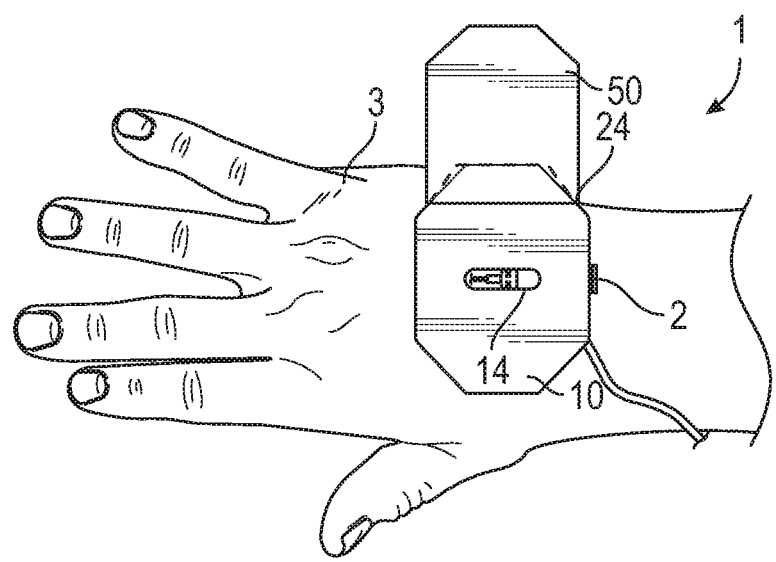

As shown in FIG. 7, once the catheter securement dressing 1 is positioned, a clinician can apply skin adhesive 60 to the catheter insertion site via the top access window 44 and the access window 14. In some cases, the positioned catheter securement dressing 1 can secure the catheter 2 to prevent unintentional dislodging of the catheter 2 during application of the skin adhesive 60. In other cases, the positioned catheter securement dressing 1 can secure the catheter 2 to free the clinician from having to hold the catheter 2 while applying the skin adhesive 60. Referring now to FIG. 8, after the skin adhesive is applied and before or after it has dried and/or set, the top release liner 40 can be removed with top release tab 42. In some cases, the top release liner 40 can prevent excess skin adhesive 60 from contacting and/or drying on the first dressing layer 10.

Figure 9:
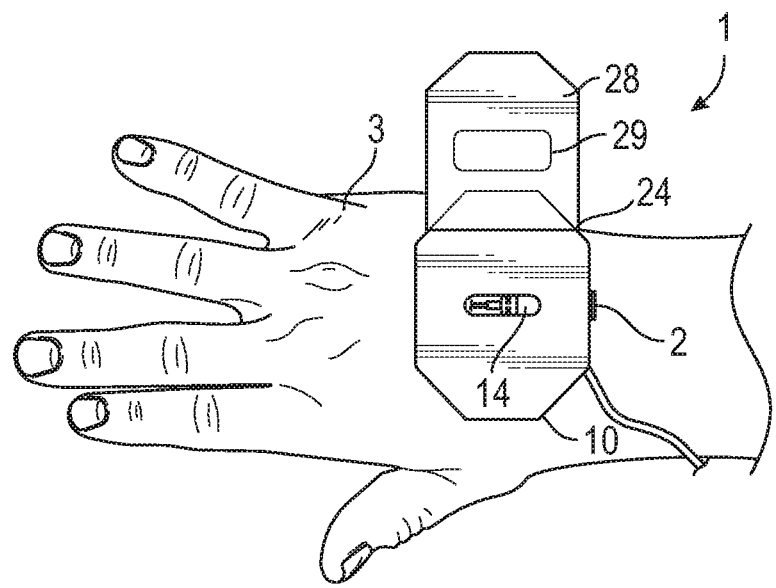
Figure 10:
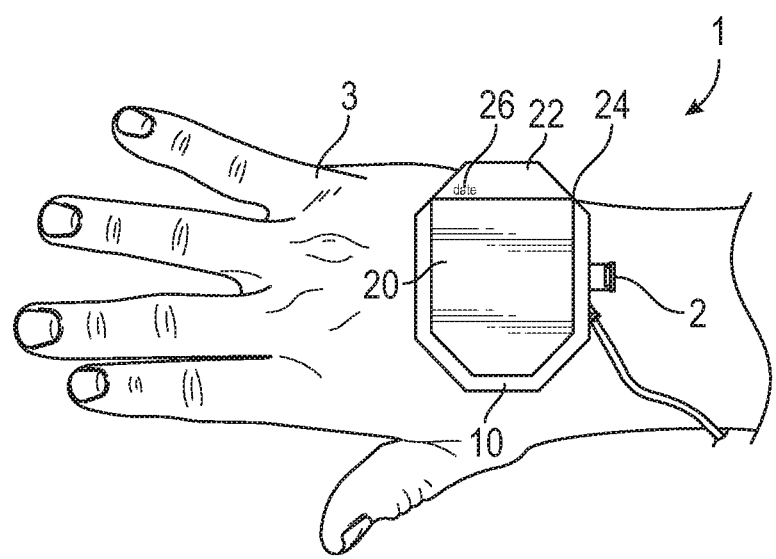

As shown in FIG. 9, the second release liner 50 can be removed with second release tab 52 to expose adhesive layer 28. In some cases, removing the second release liner 50 can expose the antimicrobial adhesive zone 29. In other cases, the second release liner 50 can prevent excess skin adhesive 60 from contacting or drying on the second dressing layer 20 and/or on adhesive layer 28. Referring now to FIG. 10, the second dressing layer 20 can be refolded along fold line 24 onto the first dressing layer 10. The second dressing layer 20 can then be pressed onto the first dressing layer 10 so that adhesive layer 28 attaches to the top surface of the first dressing layer 10 to cover the catheter insertion site. In some cases, the antimicrobial adhesive zone 29 contacts the catheter insertion site. In other cases, the clinician can then note the time and/or date that the catheter was placed on the label area 26. In other cases, the adhesive layer 28 can comprise multiple-use adhesive that allows the second dressing layer 20 to be peeled away from the first dressing layer and folded back along fold line 24 so that the clinician can inspect the catheter insertion site. After inspecting the catheter insertion site, the clinician can refold the second dressing layer 20 onto the first dressing layer 10. The second dressing layer 20 can also comprise a pull tab (not shown) to aid the clinician in peeling back the second dressing layer 20 and to aid in repositioning the second dressing layer 20 after inspection. In yet other cases, at least a portion of the second dressing layer 20 can be transparent so that the clinician can inspect the catheter insertion site without folding back the second dressing layer 20.

Figure 11:
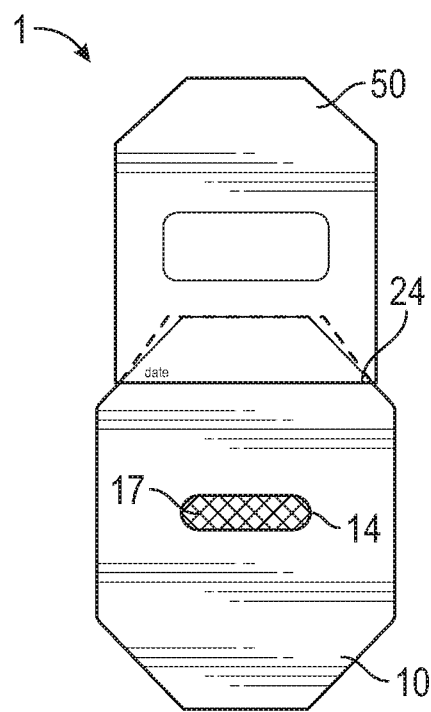
FIG. 11 illustrates a top view of an exemplary catheter securement dressing with a skin adhesive application window.

In addition to the aforementioned features, the described catheter securement dressing 1 can be modified in any suitable manner that allows it to function as intended. In one example, as shown in FIG. 11, the catheter securement dressing 1 is configured with a mesh support 17. The mesh support 17 can be configured to permit the skin adhesive 60 to pass through the mesh support 17 to reach the catheter insertion site and to provide mechanical structure so that the skin adhesive securely adheres to the first dressing layer 10 by adhering to the mesh support 17. The mesh support 17 can comprise any suitable material that allows it to function as intended, including, but not limited to, mesh bandaging, medical netting, medical gauze, plastic mesh, fibers, metal netting, and any other suitable material.

Figure 12:
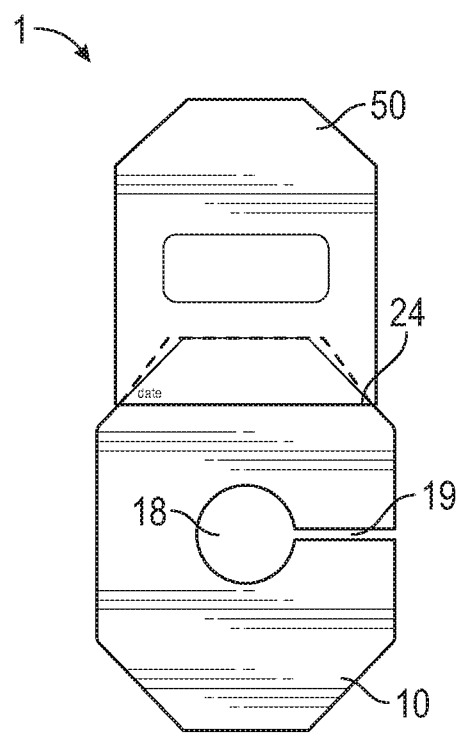
FIG. 12 illustrates a top view of an exemplary catheter securement dressing with a skin adhesive application window.

In another example, as shown in FIG. 12, the catheter securement dressing 1 can be configured with an opening 18 configured to limit the spread of the skin adhesive 60. In some cases, the opening 18 can be sized to match the size and/or shape of the catheter insertion site to limit a portion of the skin that the skin adhesive 60 can contact. The catheter securement dressing can also be configured with a slotted opening 19. The slotted opening 19 can extend from the opening 18 to an edge of the catheter securement dressing 1. The slotted opening 19 can be configured to allow the first dressing layer 10 to be fully positioned under the catheter 2. For example, the clinician can clean and prepare the catheter insertion site and can insert the catheter 2. Then the clinician can apply the catheter securement dressing 1 with the opening 18 over the catheter insertion site while passing a body of the catheter 2 through the slotted opening 19. The slotted opening 19 ends up beneath the body of the catheter 2. The clinician can then apply pressure so that the adhesive layer 16 attaches the bottom portion of the first dressing layer 10 to the skin of the patient 3. The clinician then completes the remaining steps as described above.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments, in all respects, are meant to be illustrative only and should not be construed to be limiting in any manner.

The invention claimed is:

1. A method of applying a catheter securement dressing, the method comprising:
   inserting a catheter at a catheter insertion site;
   attaching a first dressing layer of a catheter securement dressing at the catheter insertion site, wherein the catheter securement dressing comprises:
   the first dressing layer comprising an access window;
   a first adhesive layer configured to adhere the first dressing layer to skin;
   a second dressing layer; and
   a second adhesive layer configured to adhere the second dressing layer to the first dressing layer;
   applying skin adhesive to the catheter insertion site through the access window in the first dressing layer; and
   attaching the second dressing layer of the catheter securement dressing over the access window.

2. The method of claim 1, wherein attaching the first dressing layer secures the catheter at the catheter insertion site to prevent dislodging of the catheter during application of the skin adhesive.

3. The method of claim 1, further comprising removing a top release liner from the first dressing layer after applying the skin adhesive.

4. The method of claim 1, further comprising removing a bottom release liner from an adhesive layer of the first dressing layer prior to attaching the first dressing layer at the catheter insertion site.

5. The method of claim 1, further comprising removing a second release liner from an adhesive layer of the second dressing layer prior to attaching the second dressing layer over the access window.

\* \* \* \* \*